US008862227B2

(12) United States Patent
Apperson et al.

(10) Patent No.: US 8,862,227 B2
(45) Date of Patent: *Oct. 14, 2014

(54) DEFIBRILLATORS DETECTING ORIENTATION OF ELECTRODE CONNECTION TO ADJUST ENERGY DOSAGE

(71) Applicant: Physio-Control, Inc., Redmond, WA (US)

(72) Inventors: Ryan William Apperson, Bothell, WA (US); John Carlton Daynes, Redmond, WA (US); Kelly Schneiderman, Greenwood Village, CO (US)

(73) Assignee: Physio-Control, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/849,201

(22) Filed: Mar. 22, 2013

(65) Prior Publication Data

US 2013/0218220 A1    Aug. 22, 2013

Related U.S. Application Data

(63) Continuation of application No. 13/190,241, filed on Jul. 25, 2011, now Pat. No. 8,412,322.

(60) Provisional application No. 61/432,857, filed on Jan. 14, 2011.

(51) Int. Cl.
*A61N 1/18* (2006.01)
*A61N 1/39* (2006.01)
*A61N 1/04* (2006.01)

(52) U.S. Cl.
CPC ........... *A61N 1/3987* (2013.01); *A61N 1/3993* (2013.01); *A61N 1/046* (2013.01); *A61N 1/3931* (2013.01); *A61N 1/3968* (2013.01)
USPC ........................... 607/5; 607/6; 607/7; 607/8

(58) Field of Classification Search
USPC ........................................................ 607/5–8
See application file for complete search history.

(56) References Cited

U.S. PATENT DOCUMENTS

| 4,850,356 | A | 7/1989 | Heath |
| 5,080,099 | A | 1/1992 | Way et al. |
| 5,713,927 | A | 2/1998 | Hampele et al. |
| 6,101,413 | A | 8/2000 | Olson et al. |
| 6,108,578 | A | 8/2000 | Bardy et al. |
| 6,134,468 | A | 10/2000 | Morgan et al. |
| 6,560,485 | B2 | 5/2003 | Herleikson |
| 6,990,373 | B2 | 1/2006 | Jayne et al. |
| 7,016,726 | B1 | 3/2006 | Picardo et al. |
| 7,062,321 | B2 | 6/2006 | Lyster et al. |

(Continued)

*Primary Examiner* — Joseph Stoklosa
(74) *Attorney, Agent, or Firm* — Marger Johnson & McCollom, P.C.

(57) ABSTRACT

Embodiments of the present concept are directed to external defibrillators that include an electrode connection port having multiple connection options, and include a detection device to determine an electrode connection configuration so as to provide an appropriate electrical shock to a patient. The detection device detects the electrode connection configuration of a plug connector for connected electrodes to determine if the plug connector is in an adult orientation or a pediatric orientation. The external defibrillator is configured to a deliver an electrical shock with less energy when the pediatric orientation is detected rather than the adult orientation.

14 Claims, 8 Drawing Sheets

*DEFIBRILLATOR WITH PLUG DETECTION DEVICE*

(56) References Cited

U.S. PATENT DOCUMENTS 8,412,322 B2 * 4/2013 Apperson et al. ................ 607/7

2003/0055459 A1 3/2003 Lyster et al.
2005/0267536 A1 12/2005 Freeman et al.
2009/0254136 A1 10/2009 Powers

* cited by examiner

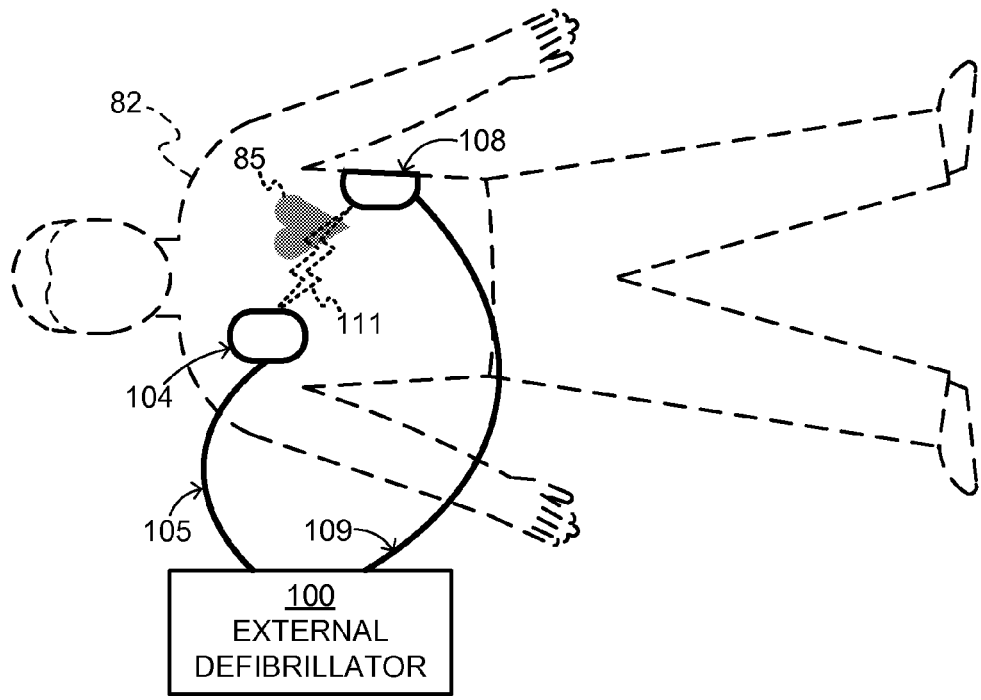
FIG. 1 *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2 *TWO MAIN TYPES OF EXTERNAL DEFIBRILLATORS*

COMPONENTS OF EXTERNAL DEFIBRILLATOR

FIG. 4  *DEFIBRILLATOR WITH PLUG DETECTION DEVICE*

FIG. 5  *DEFIBRILLATOR PORT WITH PHYSICAL DETECTION*

FIG. 6 — *DEFIBRILLATOR PORT WITH PIN DETECTION*

FIG. 7 ELECTRICAL CIRCUIT TO DETERMINE ELECTRODE PLUG CONNECTION ORIENTATION

*METHOD FOR DETERMINING ENERGY LEVEL FOR DEFIBRILLATOR ELECTRICAL CHARGE*

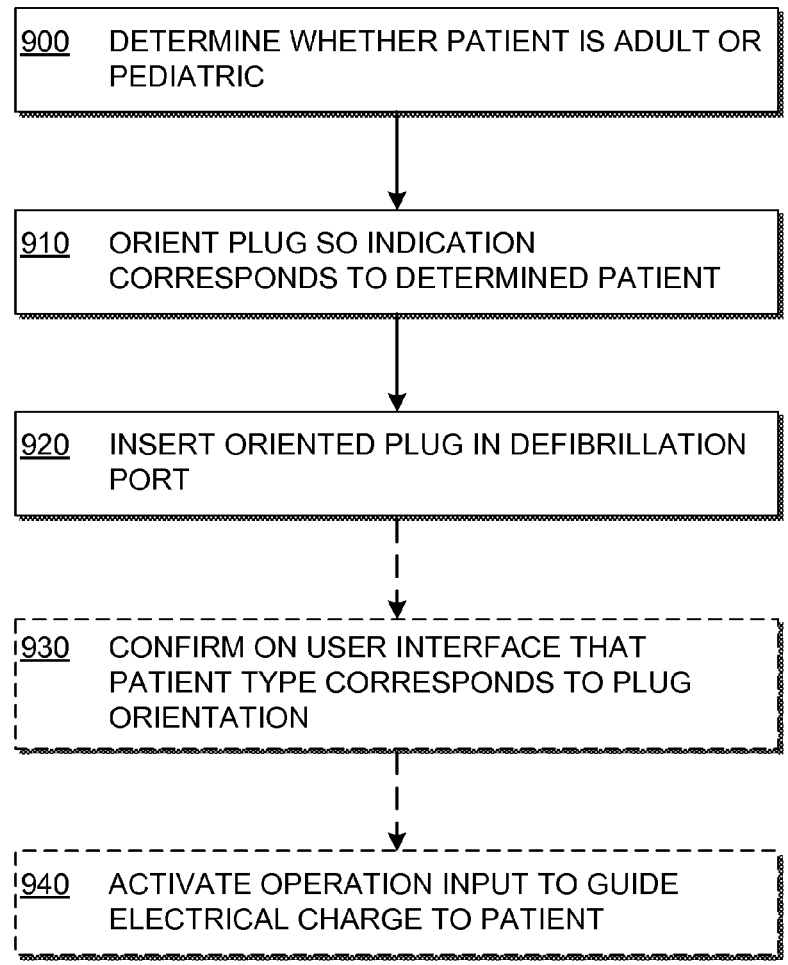
FIG. 9 — *METHOD FOR OPERATING AN EXTERNAL DEFIBRILLATOR FOR USE WITH ELECTRODES HAVING A PLUG CONNECTOR*

US 8,862,227 B2

DEFIBRILLATORS DETECTING ORIENTATION OF ELECTRODE CONNECTION TO ADJUST ENERGY DOSAGE

CROSS REFERENCE TO RELATED PATENT APPLICATIONS

This patent application is a continuation of co-pending U.S. Non-Provisional patent application Ser. No. 13/190,241, filed on Jul. 25, 2011, which claims priority to U.S. Provisional Patent Application Ser. No. 61/432,857, filed on Jan. 14, 2011.

FIELD

This invention generally relates to external defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a lifesaving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

To effectively terminate VF in a patient, the electrical shock administered by the defibrillator can be at quite high energy levels. Since a majority of patients requiring defibrillation are adults, many defibrillators are set up in a default mode to provide treatment to these types of patients. Other types of patients, however, such as pediatric patients, geriatric patients, or neonate patients, generally require significantly lower energy level shocks to terminate VF, and may be injured by the administration of a high energy level shock used for an adult.

To ensure that these other types of patients receive an electrical shock with an appropriate energy level, a rescuer may have to adjust parameters on the defibrillator prior to using the defibrillator. This adjustment requirement adds delay time to the treatment of the patient and requires that the rescuer remember to make an adjustment. Even in situations where the defibrillator requires a rescuer to input patient parameters prior to treatment, the rescuer must take time to locate an input area of the defibrillator and accurately enter observed parameters about the patient.

BRIEF SUMMARY

The present description gives instances of medical devices, systems, and methods, the use of which may help overcome problems and limitations of the prior art.

In particular, embodiments of the present concept are directed to external defibrillators that include an electrode connection port having multiple connection options, and include a detection device to determine an electrode connection configuration so as to provide an appropriate electrical shock to a patient.

In some embodiments, an external defibrillator for use with electrodes having a plug connector with at least two active pins connected to the electrodes is disclosed. The external defibrillator includes an energy storage module for storing an electrical charge, and a defibrillation port for receiving the plug connector so as to guide via the electrodes at least a portion of the stored electrical charge to a patient. The defibrillation port is structured to receive the plug connector in at least one of an adult orientation and a pediatric orientation, which is different from the adult orientation. The defibrillation port also has nodes for establishing electrical contact with the active pins of the plug connector for guiding the charge, where at least one of the nodes configured to establish electrical contact with one of the active pins in each of the adult orientation and the pediatric orientation. The external defibrillator also includes an orientation detection device structured to detect whether the plug connector is connected to the defibrillation port in the adult orientation or in the pediatric orientation, and a processor for determining when to guide the electrical charge portion. Here, if the orientation detection device detects that the plug connector is in the pediatric orientation, the portion of the charge guided via the electrodes is less than if the adult orientation had been detected.

An advantage over the prior art is that the electrode port with multiple configuration options of the external defibrillator allows for the use of the same set of electrodes for both adult and pediatric patients. In addition, a rescuer has only to correctly orient the plug connector of the electrodes to change the amount of charge delivered to a patient. This may be especially important if the rescuer is not a trained medical provider because the rescuer will not have to adjust any dials, switches, or other inputs on the defibrillator, which may be confusing to the rescuer.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 9 is a flowchart for illustrating methods of operating an external defibrillator according to embodiments.

DETAILED DESCRIPTION

Figure 3:
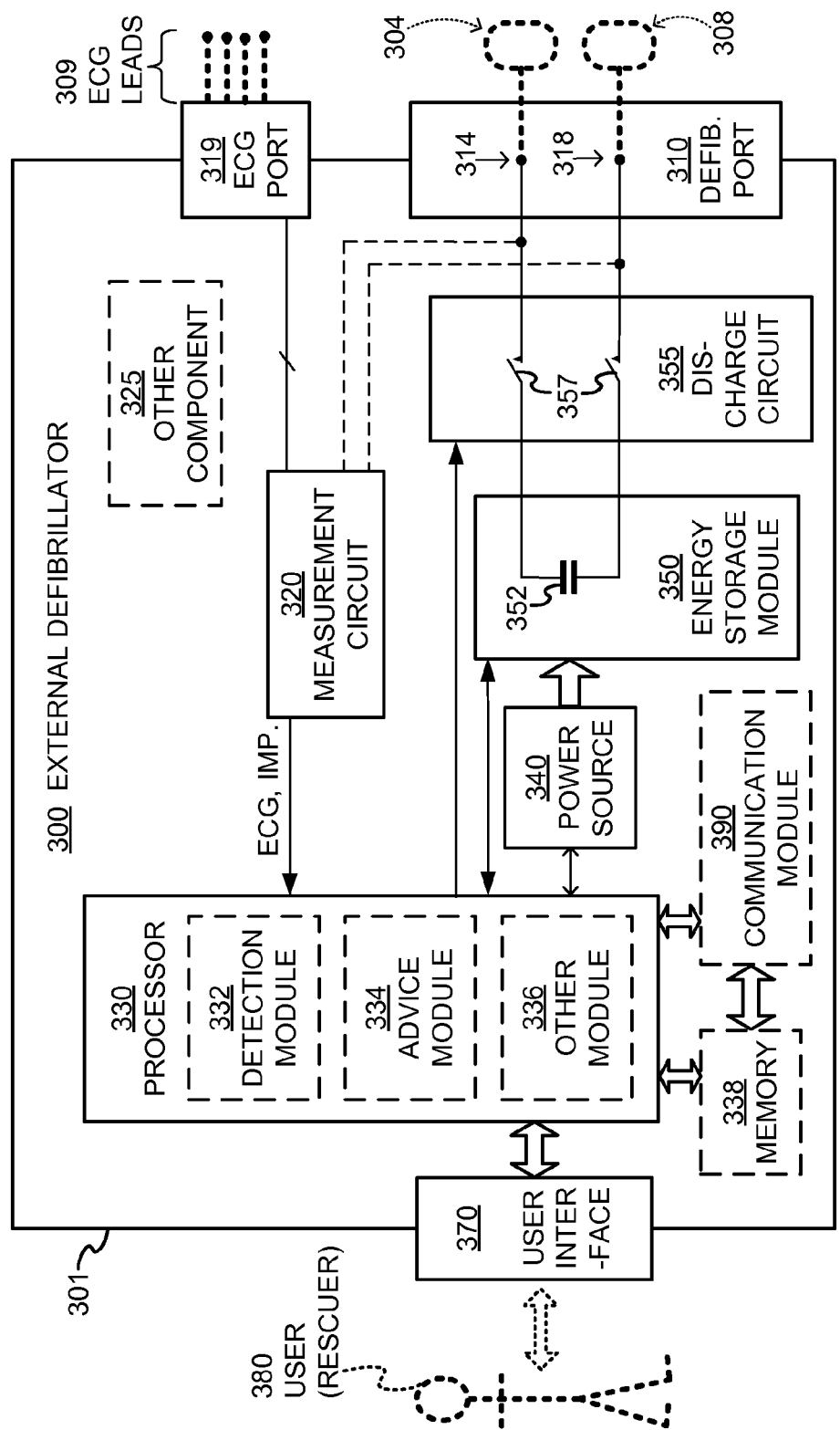
FIG. 3 is a diagram showing components of an external defibrillator, such as the one shown in FIG. 1, which is made according to embodiments.

As has been mentioned, the present description is about medical devices, systems, and methods for determining energy levels to provide to a patient from an external defibrillator.

Embodiments are now described in more detail.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing two main types of external defibrillators, and who they are primarily intended to be used by. A first type of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

FIG. 3 is a diagram showing components of an external defibrillator 300 made according to embodiments. These components can be, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and an other component 325 for the above described additional features, such as patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

Defibrillator 300 may also include another component 325. In some embodiments, component 325 is an orientation detection device, which is structured to determine an orientation of an electrode plug connector connected to the defibrillation port 310.

Figure 4:
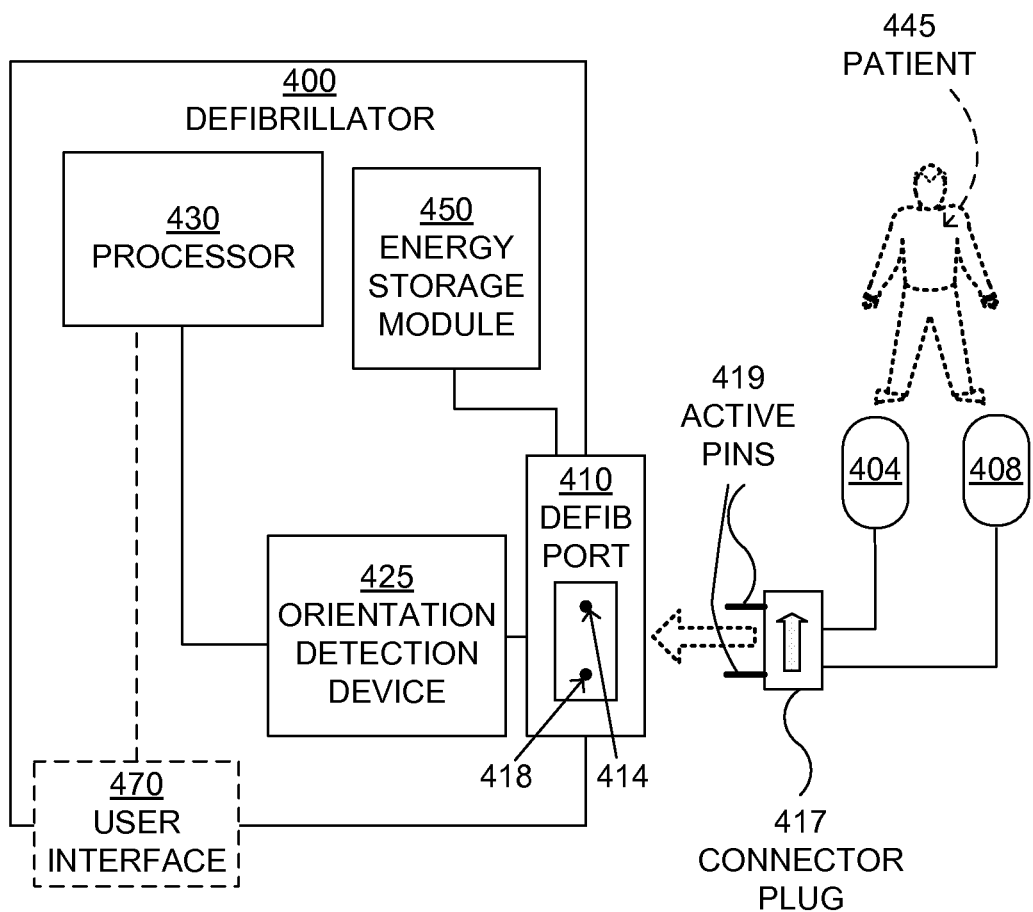
FIG. 4 is a diagram showing an external defibrillator with an orientation detection device according to embodiments.

FIG. 4 is a diagram showing an external defibrillator 400 for use with electrodes 404, 408 having a plug connector 417 with at least two active pins 419. The defibrillator 400 includes an energy storage module 450 for storing an electrical charge, and a defibrillation port 410 for receiving the plug connector 417. A portion of the electrical charge stored in the energy storage module 450 can be guided via the electrodes 404, 408 to a patient 445 to treat ventricular fibrillation in a patient. The defibrillation port 410 is structured to receive the plug connector 417 in at least two orientations, such as an adult orientation and a pediatric orientation that is different from the adult orientation. The defibrillation port 410 includes nodes 414, 418 for establishing electrical contact with the active pins 419 of the plug connector 417. At least one of the nodes 414, 418 is configured to establish electrical contact with one of the active pins 419 in each of the adult orientation and the pediatric orientation.

In some embodiments, the external defibrillator 400 may also include a user interface 470 for outputting an indication of the detected orientation. This indication may include an auditory voice signal indicating that detected orientation, such as: "Electrode configuration set for use on a child." Alternative, user prompts may be voiced so as to match the patient type corresponding to the detected orientation. That is, if the detected orientation indicates that the patient is a child, a child-like voice may provide the user prompts. The user interface 470 may also be configured to illustrate how the orientation of the plug connector 417 can be changed according to whether the patient 445 is an adult or a child. In these embodiments, the user interface 470 may include video display that outputs different words, colors, or images that correspond with a patient type corresponding to a detected orientation of the plug connector 417.

The processor 430 may be configured to determine what portion of the charge should be guided to the patient 445 via the electrodes 404, 408 in response to the detected orientation. Adjusting the amount of guided charge may, in some embodiments, be accomplished by adjusting the amount of energy stored in the energy storage module 450 prior to guiding the charge to the patient. Here, substantially all of the stored charge will be guided to the patient 445 regardless of the detected orientation of the plug connector 417. Instead, the amount of energy stored in the energy storage module 450 is modified based on the detected orientation of the plug connector 450. In one example, the processor 430 may control the amount of energy stored in the energy storage module 450 by controlling the amount of energy transferred from the power source 340 (FIG. 3) to the energy storage module 450.

In other embodiments, however, the amount of charge guided to the patient may be adjusted by restricting, shunting, or otherwise modifying the amount of energy that is transferred from the energy storage module 450 to the electrodes 404, 408. Here, the amount of energy stored in the energy storage module 450 may be similar despite what orientation is detected for the plug connector 417. The detected orientation of the plug connector 417, instead, is used to modify the charge during the transfer of the charge from the energy storage module 450 to the patient 445. In one example, the processor 430 may modify the parameters of a discharge circuit 355 (FIG. 3) based on the detected orientation of the plug connector 417 to deliver an electrical shock with a desired energy level that is appropriate for an adult.

The orientation detection device 425 may use a variety of different sensor types for detecting the orientation of the plug connector 417 in the defibrillation port 410. In some embodiments, the orientation detection device 425 includes an electrical sensor for detecting whether the plug connector 417 is connected in the adult orientation or in the pediatric orientation. In other embodiments, the orientation detection device 425 may include one or more a mechanical sensor, an electromechanical sensor, an optical sensor, a magnetic sensor, or an electromagnetic sensor for detecting whether the plug connector 417 is connected in the adult orientation or in the pediatric orientation.

If an orientation of a connected plug connector 417 is not detected by the orientation detection device 425, or the detected orientation is not recognized, the defibrillator 400 may guide a default defibrillation energy to the patient 445 via the electrodes 404, 408. An orientation may not be detected, for example, when electrodes 404, 408 are connected that have a plug connector 417 that does not trigger orientation detection by the orientation detection device 425. For example, some electrodes 404, 408 may not be optimized for delivering electrical charges to both adult and pediatric patients 445. These electrodes 404, 408 may not trigger orientation detection while more specialized electrodes 404, 408 that are structured for use on multiple patients 445 may include a connector plug 417 that allows for orientation detection by the orientation detection device 425. The default defibrillation energy may be set to any level, which may depend on the expected patient type. For example, in pediatric hospitals or day care centers, the default energy level may be set for pediatric patient 445, while airports or shopping malls may have defibrillators 400 with default energy levels set for adult patients 445.

In some embodiments, the defibrillation port 410 is structured to receive the plug connector 417 in a first orientation and a second orientation that is about 180 degrees offset from the first orientation. Here, the first orientation may correspond to an adult patient and the second orientation that is 180 degrees offset may correspond to a pediatric patient.

In other embodiments, the defibrillation port 410 is structured to receive the plug connector in a first orientation, a second orientation, a third orientation, and fourth orientation, where each orientation is offset about 90 degrees from two other orientations, and offset about 180 degrees from the remaining orientation. Here, there are four possible orientations that may account for an expanded list of patient types. For example, in addition to the adult and pediatric patients, which correspond to the first and second orientation, the processor 430 may further determine an energy level appropriate for a neonate patient 445 when the plug connector 417 is determined to be in a third orientation, and determines an energy level appropriate for a geriatric patient 445 when the plug connector 417 is determined to be in a fourth orientation.

To facilitate ease of connection, the defibrillation port 410 may include a visible indication identifying a patient type associated with each connection orientation for an electrode plug connector 417. For example, the visible indication may include a first color that is associated with a first connection orientation and a second color is associated with a second connection orientation. In addition, the visible indication on the defibrillation port 410 may correspond to at least one visible indication on the electrode plug connector 417.

In some embodiments, the defibrillation port 410 may include three nodes 414, 418 to connect to two active pins 419 of a plug connector 417. Here, a first and a second of the active pins 419 establish contact with a first and a second of the nodes 414, 418 respectively in the adult orientation, and the first and the second active pins 419 establish contact with the first node and a third node 414, 418 respectively in the pediatric orientation. In some of these embodiments, the first active pin 419 could have a square cross section, and the second active pin 419 could have a triangular cross section. Here the defibrillation port has a central opening that is square in shape for the first active pin, and is flanked by two triangular openings, one of which to receive the second active pin.

In others of these embodiments, the defibrillation port 410 includes a receptacle that prevents the first active pin 419 from being received so as to make contact with the first node or the third node 414, 418. Here, the receptacle may include an open frame that is slideable within the housing to expose either the first and second openings, or expose the first and third openings. The slideable frame would thus obstruct the opening that is not to be used.

Figure 5:
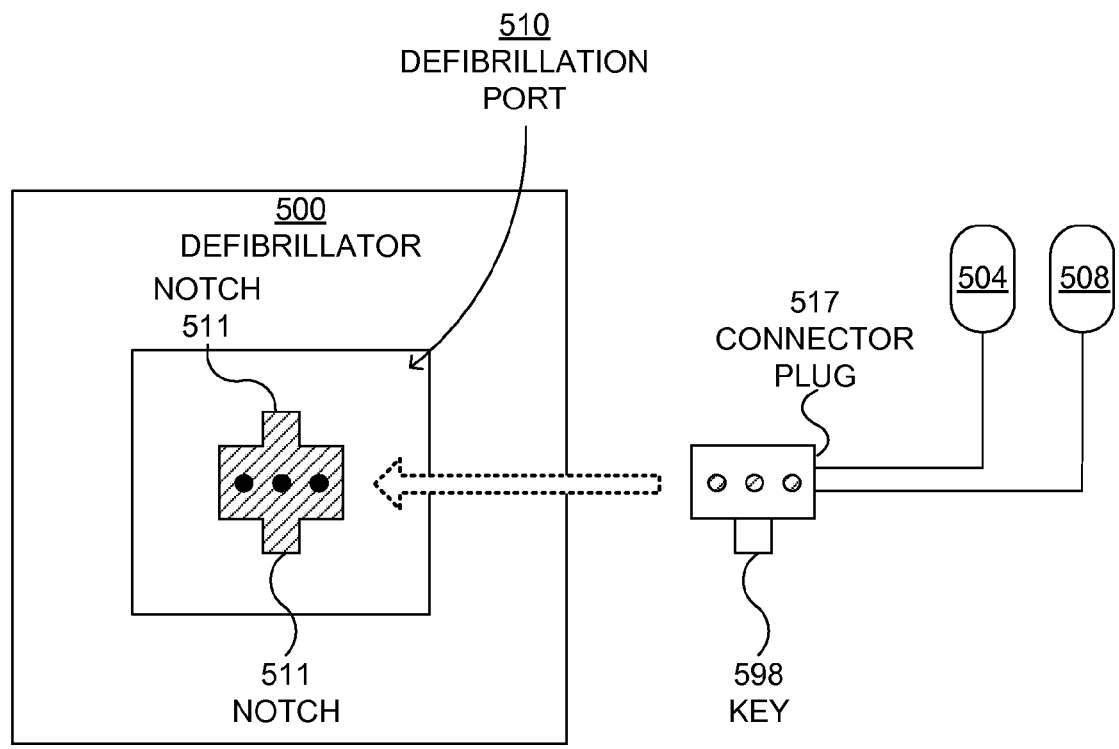
FIG. 5 is a diagram showing an external defibrillator with a keyed defibrillation port according to embodiments.

FIG. 5 is a diagram showing an external defibrillator 500 with a keyed defibrillation port 510 according to embodiments. In particular, defibrillation port 510 includes notches 511 that correspond to a physical portion or key 598 of a plug connector 517 that is connected to electrodes 504, 508. Here, the plug connector 517 may be inserted into the defibrillation port 510 with the key 598 oriented downward to treat a first type of patient, such as an adult patient. On the other hand, the plug connector 517 may be inserted into the defibrillation port 510 with the key 598 oriented upward to treat a second type of patient, such as a pediatric patient. The orientation detection device 425 (FIG. 4) in these embodiments is structured to sense the physical portion or key 598 of the plug connector 517 for detecting whether the plug connector is connected in the adult orientation or in the pediatric orientation. When a plug connector that does not include a key is connected to the defibrillation port 510, the orientation detection device 425 may not detect an orientation of the plug connector and a default energy level may be provided to the patient as discussed above. Although a defibrillation port 510 and plug connector 517 are shown in FIG. 5 with one type of physical orientation interface (i.e., the key 598 and notches 511), many different variations are possible including variations that allow for three or more orientation positions for the plug connector 517 relative to the defibrillation port 510.

Figure 6:
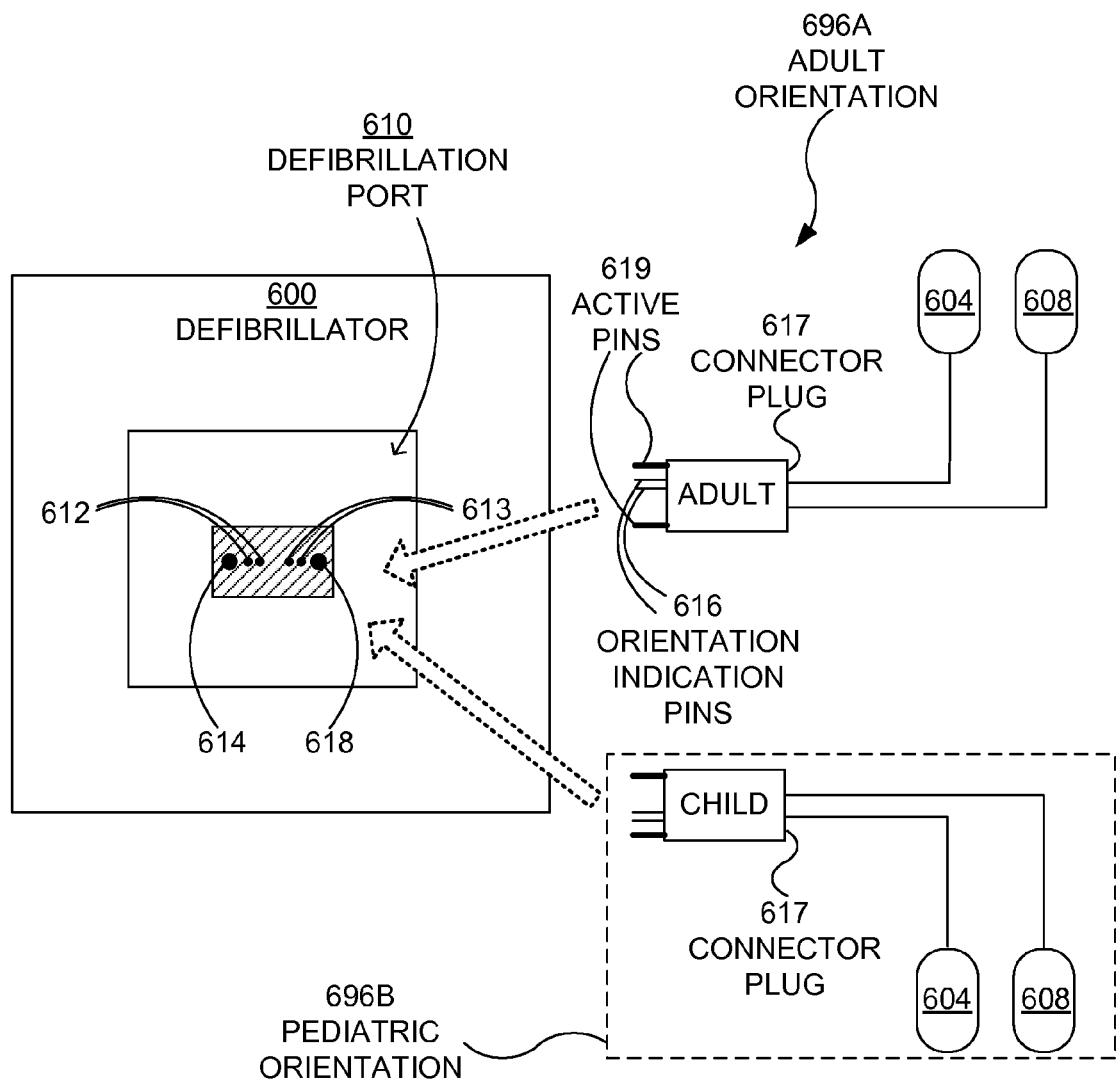
FIG. 6 is a diagram showing an external defibrillator with a defibrillation port having a pin orientation detection device according to embodiments.

FIG. 6 is a diagram showing an external defibrillator 600 with a defibrillation port 610 that utilizes another orientation detection methodology according to embodiments. Here, the defibrillation port 610 includes a first active node 614, a second active node 618, a first set of orientation nodes 612, and a second set of orientation nodes 613. The first and second active nodes 614, 618 establish electrical contact with active pins 619 of a plug connector 617 when the plug connector is connected to the defibrillator 600. Here, the first and second active pins 619 establish contact with first and second nodes 614, 618 of the defibrillation port 610 respectively in the adult orientation 618A, and the first and second active pins establish contact with the second and first nodes respectively in the pediatric orientation 618B. The active pins 619 of the plug connector 617 are connected to electrodes 604, 608 to provide a pathway to guide the electrical shock from the defibrillator 600 to the patient.

In addition, the plug connector 617 includes at least one orientation indication pin 616 in addition to the active pins 619. The orientation detection device 425 (FIG. 4) is structured to detect whether the plug connector 617 is connected in the adult orientation 696A or in the pediatric orientation 696B by sensing a location of the orientation indication pin 616 with respect to the active pins 619.

In the embodiment illustrated in FIG. 6, the plug connector 617 also includes orientation indication pins 616 that electrically contact either the first set of orientation nodes 612 or the second set of orientation nodes 613 depending on the orientation of the plug connector with respect to the defibrillation port 610. That is, in an adult orientation 696A, the orientation indication pins 616 of the plug connector 617 contact the second set of orientation nodes 613. On the other hand, in a pediatric orientation 696B, the orientation indication pins 616 contact the first set of orientation nodes 612.

Figure 7:
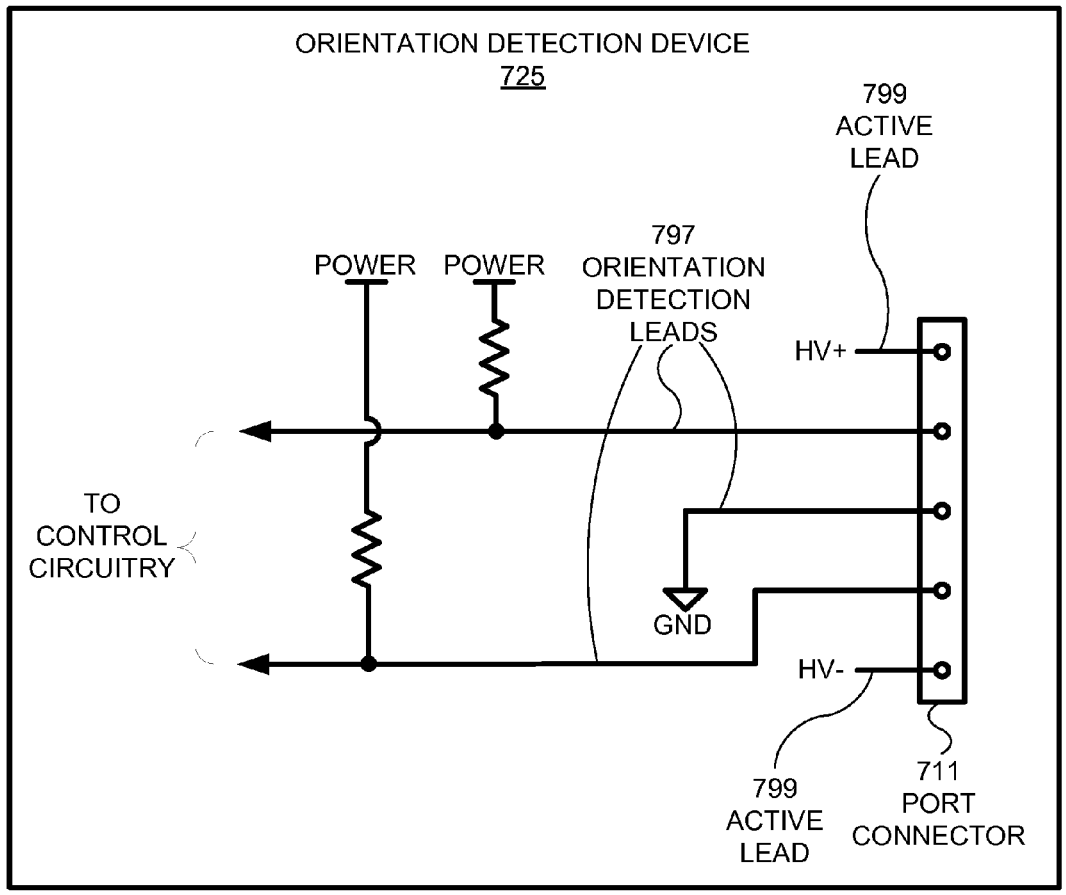
FIG. 7 is a circuit diagram for an example circuit in the orientation detection device shown in FIG. 4 according to embodiments.

FIG. 7 is a circuit diagram for an example circuit in the orientation detection device 725 according to embodiments. Referring to FIG. 7, the orientation detection device 725 includes a circuit having at least two orientation detection leads 797 for sensing an orientation indication pin of a plug connector. Here, the circuit is configured to detect an adult orientation when a first one of the orientation detection leads 797 senses the orientation indication pin, and is configured to detect a pediatric orientation when a second one of the orientation detection leads 797 senses the orientation indication pin. In one configuration, the first and second orientation detection leads 797 are structured to sense the orientation indication pin when a circuit pathway is completed with a reference pin. The reference pin can be any pin, such as a power supply pin, etc. In this example, the reference pin is ground pin 797.

Active leads 799 are structured to electrically connect with first and second active nodes of a defibrillation port 410 (FIG. 4). The active leads 799 and orientation detection leads 797 may terminate at a port connector 711 that is structured to connect with the defibrillation port 410. The active leads 799 may bypass any additional control circuitry in the orientation detection device 725 and connect to the energy storage module 450 (FIG. 4), or may entirely bypass the orientation detection device to connect to the energy storage module. The orientation detection leads 797 may connect to control circuitry in the orientation detection device 725 or connect directly to the processor 430 (FIG. 4).

Figure 8:
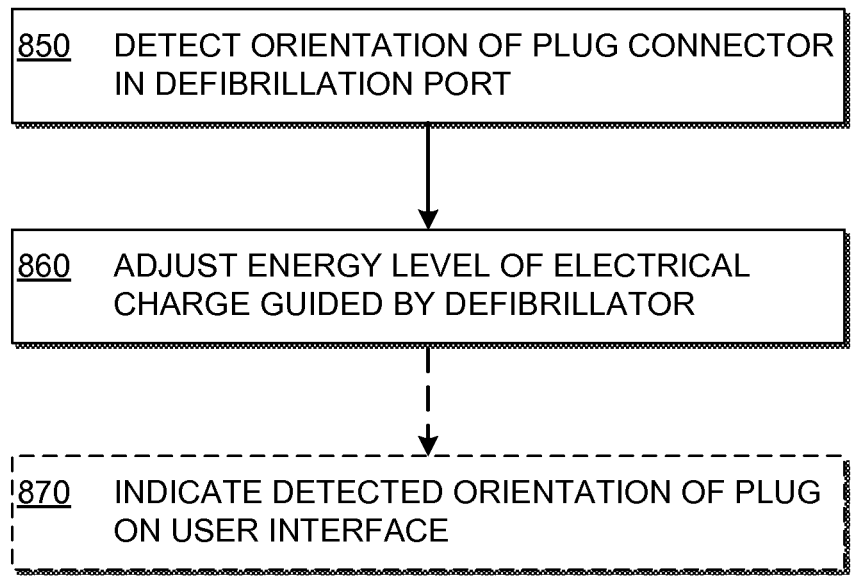
FIG. 8 is a flowchart for illustrating methods for determining an energy level for a stored electrical change in an external defibrillator according to embodiments.

FIG. 8 is a flowchart for illustrating methods for determining an energy level for a stored electrical change in an external defibrillator according to embodiments. Although this flowchart illustrates a variety of operations in a particular order, these operations may be carried out in different orders to achieve similar results in other method embodiments. In particular, FIG. 8 illustrates a method of determining an energy level for an electrical charge being guided from an external defibrillator to a patient through at least one electrode having a plug connector connected to a defibrillation port of the external defibrillator. The method shown in this illustrated flow chart may be practiced, for example, by the defibrillator 400 shown in FIG. 4.

According to an operation 850, one of more than one possible orientations of the plug connector in the defibrillation port may be detected. Each of the possible orientations of the plug connector may correspond to a defined patient type. In some embodiments, this operation may include sensing a physical portion of the plug connector. The physical portion of the connector may be sensed by a mechanical sensor, by an electrical sensor, by an optical sensor, by a magnetic sensor, or by a combination of any of the sensor types.

In other embodiments, this operation may include determining a connection location for an orientation indication pin of the plug connector. Determining a connection location may include determining which of at least two circuit pathways is completed by the orientation indication pin.

According to another operation 860, the energy level of the electrical charge guided by the external defibrillator is adjusted based on the detected orientation of the plug connector. In some embodiments, this operation may include adjusting the energy level of the guided electrical charge to a first level when the detected orientation of the plug connector corresponds to an adult patient, and adjusting the energy level of the guided electrical charge to a second level when the detected orientation of the plug connector corresponds to a pediatric patient. As discussed above, adjusting the energy level of the guided electrical charge may be accomplished by adjusting the amount of energy stored in an energy storage module of the defibrillator, or may be accomplished by adjusting the amount of energy transmitted from the energy storage module to the patient. The second level may be less than the first level so that the pediatric patient does not receive an electrical charge that is intended for a larger adult patient. Additionally, this process may include adjusting the energy level of the guided electrical charge to a default level when the detected orientation of the plug connector is not defined.

According to an optional operation 870, an indication of the detected orientation may be outputted on a user interface of the external defibrillator. As discussed above, this indication may include auditory signals, visual signals, or a combination of the two. In addition, this process may include providing instructions on providing treatment to the type of patient associated with the detected orientation. For example, these instructions may provide methods for placing the electrodes on the patient or other important information.

FIG. 9 is a flowchart for illustrating methods of operating an external defibrillator according to embodiments. Although this flowchart illustrates a variety of operations in a particular order, these operations may be carried out in different orders to achieve similar results in other method embodiments. In particular, FIG. 9 illustrates a method of operating an external defibrillator for use with electrodes having a plug connector with at least two active pins connected to the electrodes, where the plug connector includes at least one indication corresponding to a patient category. The method shown in this illustrated flow chart may be practiced, for example, on the defibrillator 400 shown in FIG. 4.

According to an operation 900, a determination is made as to whether the patient fits into an adult patient category or into a pediatric patient category. Here, a rescuer may make the determination based on observing the patient. If the patient is a teenager, the rescuer may initially treat the patient as a pediatric patient and subsequently treat the patient as an adult patient if the patient is not revived by the pediatric procedures.

According to another operation 910, the plug connector is oriented so that the indication corresponds to the determined patient category. Here, the plug connector may be rotated or otherwise manipulated so that it is positioned correctly relative to the defibrillator. According to another operation 920, the oriented plug is inserted in a defibrillation port of the external defibrillator.

In an optional operation 930, the patient type corresponding to the orientation of the inserted plug connector is confirmed on a user interface of the defibrillator. Here, for example, a defibrillator may detect that the plug connector is inserted in a pediatric orientation and request that the rescuer confirm that the patient is a child. The rescuer may in turn utilize the user interface of the defibrillator to make this confirmation or otherwise correct the orientation of the connector plug.

In another optional operation 940, an operation input on the external defibrillator is activated to guide a portion of a stored electrical charge to the connected electrodes. Here, the guided portion of the electrical change corresponds to the orientation of the plug connector.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

What is claimed is:

1. An external defibrillator for use with electrodes having a plug connector, the external defibrillator comprising:
    an energy storage module for storing an electrical charge;
    a defibrillation port structured to guide via the electrodes at least a portion of the stored electrical charge to a patient;
    a receiver structured to receive the plug connector of the electrodes;
    a detector coupled to the receiver and structured to determine whether the plug connector is inserted into the receiver in a first orientation or the plug connector is inserted into the receiver in a different second orientation;
    a processor coupled to the detector and structured to cause the defibrillation port to guide a first defibrillation energy via the electrodes when the detector determines that the plug connector is inserted into the receiver in the first orientation, and structured to cause the defibrillation port to guide a second defibrillation energy via the electrodes when the detector determines that the plug connector is inserted into the receiver in the second orientation, the first defibrillation energy greater than the second defibrillation energy.

2. The external defibrillator according to claim 1, in which the first orientation is an adult orientation and the second orientation is a pediatric orientation.

3. The external defibrillator of claim 1, further comprising:
    a user interface for outputting an indication of the detected orientation.

4. The external defibrillator of claim 1, further comprising:
    a user interface illustrating how the orientation can be changed according to whether the patient is an adult or a child.

5. The external defibrillator of claim 1, in which
    the receiver is a portion of the defibrillation port and includes nodes for establishing electrical contact with active pins in the plug connector.

6. The external defibrillator of claim 5, in which
    the plug connector includes a first and a second of the active pins structured to establish electrical contact with a first and a second of the nodes respectively in the first orientation, and the first and the second active pins establish contact with the second and the first nodes respectively in the second orientation.

7. The external defibrillator of claim 5, in which
a first and a second of the active pins establish contact with a first and a second of the nodes respectively in the first orientation, and the first and the second active pins establish contact with the first node and a third node respectively in the second orientation.

8. The external defibrillator of claim 7, in which
the defibrillation port includes a receptacle that prevents the first active pin from being received so as to make contact with the first node or the third node.

9. The external defibrillator of claim 1, in which
the detector is structured to sense a physical portion of the plug connector for detecting whether the plug connector is connected in the first orientation or in the second orientation.

10. The external defibrillator of claim 1, in which
the detector includes at least one of a mechanical sensor, electrical sensor, electromechanical sensor, optical sensor, or magnetic sensor for detecting whether the plug connector is connected in the first orientation or in the second orientation.

11. The external electrode of claim 1, in which
a portion of the charge guided via the electrodes corresponds to a default defibrillation energy when the detector does not detect that the plug connector is connected in the first orientation or in the second orientation.

12. The external defibrillator of claim 1, in which
the plug includes at least one orientation indication pin in addition to the active pins, and
the detector is structured to detect whether the plug connector is connected in the first orientation or in the second orientation by sensing a location of the orientation indication pin with respect to the active pins.

13. The external defibrillator of claim 12, in which
the detector further includes a circuit having at least two orientation detection leads for sensing the orientation indication pin of the plug, the circuit configured to detect the first orientation when a first one of the orientation detection leads senses the orientation indication pin and configured to detect the second orientation when a second one of the orientation detection leads senses the orientation indication pin.

14. The external defibrillator of claim 13, in which
the first and second orientation detection leads are structured to sense the orientation indication pin when a circuit pathway is completed with a reference pin.

* * * * *